United States Patent [19]

Ascher et al.

[11] Patent Number: 5,138,049
[45] Date of Patent: Aug. 11, 1992

[54] CEPHALOSPORIN DERIVATIVE

[75] Inventors: Gerd Ascher, Kundl; Hubert Sturm, Innsbruck, both of Austria

[73] Assignee: Biochemie, Tyrol, Austria

[21] Appl. No.: 643,879

[22] Filed: Jan. 18, 1991

[30] Foreign Application Priority Data

Jan. 22, 1990 [AT] Austria ................................. 128/90

[51] Int. Cl.5 .................. C07D 501/16; A61K 31/545
[52] U.S. Cl. .................................................. 540/227
[58] Field of Search ........................ 540/227, 226, 221

[56] References Cited

U.S. PATENT DOCUMENTS 4,927,922  5/1990  Lee et al. ............................ 540/227

Primary Examiner—Nicholas S. Rizzo
Attorney, Agent, or Firm—Gerald D. Sharkin; Robert S. Honor; Thomas O. McGovern

[57] ABSTRACT

The invention relates to a nitrate of (6R,7R)-7-{[2-(2-amino-4-thiazolyl)]-2-oxoacetamido}-3-(1,2,3-thiadizol-5-yl)thiomethyl-3-cephem-4-carboxylic acid, a process for its production and its use.

1 Claim, No Drawings

CEPHALOSPORIN DERIVATIVE

This invention relates to (6R,7R)-7-{[2-(2-amino-4-thiazolyl)]-2-oxoacetamido}-3-(1,2,3-thiadiazol-5-yl)-thiomethyl-3-cephem-4-carboxylic acid of formula I

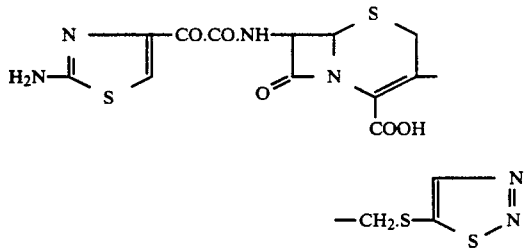

the nitrate form thereof, processes for the production of the nitrate and its use, e.g. in the production or cephalosporin antibiotics, especially (6R,7R)-7-{[2-(2-amino-4-thiazolyl]-(Z)-2-[oxyimino]acetamido}-3-(1,2,3-thiadiazol-5-yl)thiomethyl-3-cephem-4-carboxylic acids such as KP 736 and cefuzonam.

The nitrate of the compound of formula I is new and forms part of the present invention.

It has now been found that the compound of formula I in an aqueous medium surprisingly forms a poorly soluble, crystalline nitrate. Isolation of the nitrate may be effected by simple filtration from the acylation mixture, whereby by-products and impurities remain in the solution. This nitrate is stable and opens up the way for the production of derivatives of the compound of formula I in high yield and in high purity using mild conditions. The nitrate may be produced by reacting a compound of formula I with nitric acid or a nitrate salt.

The nitrate of the compound of formula I may for example be obtained by addition of an alkali or earth alkali metal nitrate to an acidic solution of the compound of formula I. If desired it may be produced using dilute nitric acid.

Preferably the compound of formula I can be obtained by reacting a compound of formula II

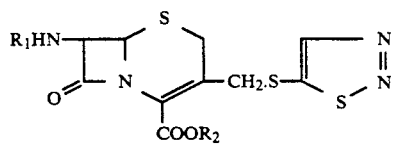

wherein either $R_1$ is hydrogen and $R_2$ is hydrogen or a cation or $R_2$ is trimethylsilyl and $R_1$ is hydrogen or trimethylsilyl with a compound of formula III

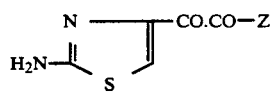

wherein Z is a leaving group, e.g. —SR, wherein R is 2-benzthiazolyl or 2-pyridyl.

The process may be carried out in accordance with known methods.

For example, the compound of formula II, wherein $R_1$ signifies hydrogen, is dissolved or suspended in a solvent which is inert under the reaction conditions, e.g. in a chlorinated hydrocarbon such as dichloromethane, and preferably introducing then the protecting group, for example by a reaction with N,O-bis-(trimethylsilyl)acetamide. The compound of formula II can however also be used in unprotected form. The reaction of the protected compound of formula II with the compound of formula III may take place directly in the reaction solution obtained, preferably at a low temperature, e.g. at about −10° C. The end compound of formula I may be isolated from the reaction mixture by known methods.

The crystalline nitrate of the compound of formula I may e.g. be obtained by reacting 7-amino-3-(1,2,3-thiadiazol-5-yl)thiomethyl-3-cephem-4-carboxylic acid with an alkali metal hydroxide or an organic nitrogen base such as triethylamine, diazabicycloundecene or tetramethylguanidine, in an aqueous organic medium, with a compound of formula III, and subsequently reacting the resultant acid of formula I with nitric acid or a nitrate salt.

Suitable organic solvents are ketones, e.g. acetone or methylisobutylketone, nitriles, e.g. acetonitrile, alcohols, e.g. ethanol or methanol, or also chlorinated hydrocarbons, e.g. methylene chloride. The nitrate of the compound of formula I may be obtained in high yield and high purity.

The present invention provides in another aspect the use of the compound of formula I in the production of cephalosporin derivatives.

In another aspect the present invention provides a process for the production of (6R,7R)-7-{[2-(2-amino-4-thiazolyl)]-2-oxoacetamido}-3-(1,2,3-thiadiazol-5-yl)thiomethyl-3-cephem-4-carboxylic acid which comprises reacting the nitrate of the compound of formula I with a base.

The free compound of formula I may be obtained by suspending the nitrate in water or in an aqueous organic medium and neutralising with an inorganic or organic base, e.g. with sodium hydroxide or triethylamine.

The present invention in another aspect provides a process for the production of (6R, 7R)-7-{[2-(2-amino-4-thiazolyl)]-(Z)-2-[oxyimino]acetamido}-3-(1,2,3-thiadiazol-5-yl)thiomethyl-3-cephem-4-carboxylic acid with comprises reacting (6R, 7R)-7-{[2-(2-amino-4-thiazolyl)]-2-oxoacetamido}-3-(1,2,3-thiadiazol-5-yl)-thiomethyl-3-cephem-4-carboxylic acid with an oxyamine derivative.

If desired the starting material may be used as such or in nitrate form. The reaction may be effected in conventional manner for the condensation of a ketone with an appropriate oxyamine or a salt thereof. The reaction may be carried out in an organic solvent, e.g. dimethylacetamide, or acetonitrile. The reaction may also be carried out in the presence of an inorganic or organic base such as an alkali metal bicarbonate, tri(lower)alkylamine, pyridine, N-(lower)alkylmorpholine, N,N-di(lower)-alkylbenzylamine, or the like. The reaction temperature is not critical and the reaction is usually carried out under cooling or at ambient temperature.

More specifically, the compound of formula I may be converted by reaction with an oxyamine derivative such as 2-aminoxymethyl-1,5-dihydroxy-4-pyridone to give KP 736, a highly effective cephalosporin antibiotic. KP 736 belongs to the new class of catechol cephalosporins having the following structure:

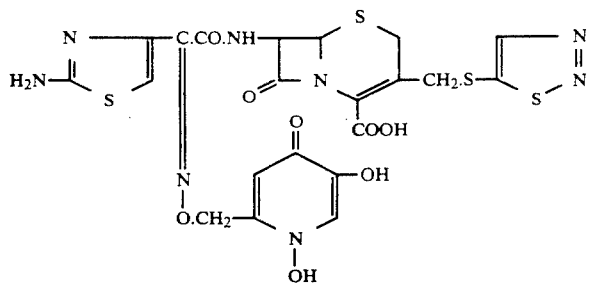

This cephalosporin is characterized by a wide spectrum of activity against gram-positive and gram-negative bacteria (including Pseudomonas) and an increased anti-bacterial activity. KP-736 possesses higher antibacterial activity against gram-negative bacteria than ceftazidime, cefotaxime and cefpirome. Preparation of KP-736 is usually effected by means of protected intermediate steps with protecting groups at the amino group of the thiazole ring, protecting groups at the γ-pyridone moiety of the oxime side chain, as well as an ester protecting group at the carboxylic acid group of the cephalosporin nucleus. The following route of synthesis has been previously described e.g. in EPA 251 299: 7-amino-3-chloromethyl-3-cephem-4-carboxylic acid-p-methoxybenzylester is reacted with 2-(2-tritylaminothiazol-4-yl)-(Z)-2-(1,5-dibenzhydryloxy-4-pyridon-2-yl-methoximino)acetic acid benzotriazole ester to form (6R, 7R)-7-[2-(2-tritylaminothiazol-4-yl)-(Z)-2-(1,5-dibenzhydryloxy-4-pyridon-2-yl-methoximino)acetamido]-3-chloromethyl-3-cephem-4-carboxylic acid-p-methoxybenzyl ester, which after complicated purification by chromatography on silica gel is reacted with 1,2,3-thiadiazole-5-thiol to form the protected end product. After cleavage of the protecting groups under acid catalysis, the end product is isolated as the trifluoroacetate. According to a similar variant of synthesis, 2-(2-formylaminothiazol-4-yl)-(Z)-2-(1,5-dibenzyloxy-4-pyridon-2-yl-methoximino)acetic acid is acylated with 7-amino-(1,2,3-thiazol-5-yl)thiomethyl-3-cephem-4-carboxylic acid-p-methoxybenzyl ester, and the protecting groups are subsequently removed under acid catalysis.

The method using the compound of formula I according to the invention is much more economical and shorter, since no complicated protecting group technology is necessary, and nor are any chromatographic purification steps involved. While column chromatography is convenient for purifying and separating chemical compounds on a laboratory scale, it is inconvenient, time-consuming and labour-intensive at the scale of a pilot or production plant. Moreover, the silica gel used for column chromatography is costly.

A further example of an antibiotic which can be produced using the nitrate of the compound of formula I is cefuzonam of formula nitrate can be converted to cephalosporin antibiotics in high yield and purity optionally via the free compound. For example KP 736 or cefuzonam can be obtained by condensation with an oxyamine derivative, e.g. 2-aminoxymethyl-1,5-dihydroxy-4-pyridone or methoxyamine or a salt thereof, a reaction which can be effected economically without using protecting groups.

In the following examples, which illustrate the invention more fully but in no way limit its scope, all temperatures are given in °C.

EXAMPLE 1

(6R,7R)-7-{[2-(2-amino-4-thiazolyl)]-2-oxoacetamido}-3-(1,2,3-thiadiazol-5-yl)thiomethyl-3-cephem-4-carboxylic acid. $HNO_3$ 33 g of 7-amino-3-(1,2,3-thiadiazol-5-yl)thiomethyl-3-cephem-4-carboxylic acid are suspended in 300 ml of aqueous acetonitrile (50% by volume), and brought to a solution by adding 16.7 ml of triethylamine. The solution is cooled to −10° and 47.8 g of 2-(2-aminothiazol-4-yl)-2-oxothioacetic acid-S-benzothiazol-2-yl-ester are added. After stirring for two hours at −10°, 100 ml of water are added. The slightly cloudy solution is filtered until clear and extracted twice with respectively 200 ml of ethyl acetate. The ethyl acetate phases are washed with 200 ml of water, the aqueous phases combined and stirred into 1000 ml of diluted nitric acid at 20° to 25°, whereby the end product crystallises. The crystal suspension is cooled to 0° and stirred for 2 hours at this temperature. The light yellow crystalline title compound is filtered off by suction and washed with water and isopropanol. After drying under vacuum, the title compound is obtained as a light yellow powder. Yield 98.5%. M.p.: from 165° (decomp.).

$^1$H-NMR (DMSO-$d_6$): 3.65 (2H, AB, $H_2$ and $H_2'$); 4.27 (2H, AB, $CH_2$-S-thiadiazole); 5.21 (1H, d, $H_6$, J=4.8 Hz); 5.61 (1H, dd, $H_7$, J=8 Hz, J=4.8 Hz); 8.10 (1H, s, thiazolyl-H); 8.90 (1H, s, thiadiazolyl-H); 9.90 (1H, d, CO—NH—, J=8 Hz).

EXAMPLE 2

(6R,7R)-7-{[2-(2-amino-4-thiazolyl)]-2-oxoacetamido}-3-(1,2,3-thiadiazol-5-yl)thiomethyl-3-cephem-4-carboxylic acid

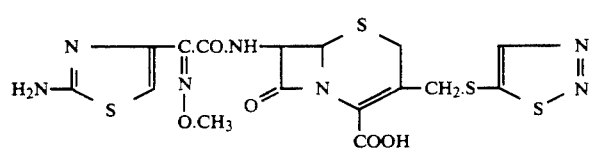

which can be obtained by reacting the compound of formula I with methoxyamine or a salt thereof. Thus the 10 g of (6R,7R)-7-[2-(2-amino-4-thiazolyl)-2-oxoacetamido]-3-(1,2,3-thiadiazol-5-yl)thiomethyl-3- cephem-4-carboxylic acid. HNO₃ are suspended in 100 ml of water. 1.5 g of NaHCO₃ are added in portions at 20° to 24°. The reaction mixture is stirred for 1 hour at 20° to 24° and then cooled to 0°. After stirring for one hour at 0°, the crystalline title compound is filtered off by suction, washed with water and isopropanol and dried under vacuum. The title compound is obtained as a light yellow crystalline powder. M.p.: from 160° (decomp.).

¹H-NMR: (DMSO-d₆): 3.63 (2H, AB); 4.25 (2H, AB); 5.22 (1H, d, J=4.5 Hz); 5.71 (1H, dd, J=4,5 Hz, J=8 Hz); 7.35 (2H, broad); 7.8 (1H, s); 8.83 (1H, S); 9.76 (1H, d, J=8 Hz).

EXAMPLE 3

(6R,7R)-7-{[2-(2-amino-4-thiazolyl)]-(Z)-2-[(1,5-dihydroxy-4-pyridon-2-yl)methoximino]acetamido}-3-(1,2,3-thiadiazol-5-yl)thiomethyl-3-cephem-4-carboxylic acid.triethylammonium salt 1.3 g of dimethylacetamide.HCl are added at 0° to a suspension of 2.91 g of {(6R,7R)-7-{[2-(2-amino-4-thiazolyl)]-2-oxoacetamido}-3-(1,2,3-thiadiazol-5-yl)thiomethyl-3-cephem-4-carboxylic acid and 1.25 g of 2-aminoxymethyl-1,5-dihydroxy-4-pyridone in 14 ml of dimethylacetamide. After stirring for 24 hours at 0°, the reaction solution is diluted with 14 ml of acetonitrile and then added in drops to 100 ml of acetonitrile, whereby the pH of the precipitating suspension is maintained at 7.0 by simultaneously adding in drops triethylamine. The suspension is stirred for 1 hour in an ice bath. Then the deposit is filtered off by suction and washed with acetonitrile. After drying under vacuum, the title compound is obtained as a light yellow coloured powder.

¹H-NMR (D₂O/K₂CO₃): 1.24 (9H, t, J=7.2 Hz, —CH₂—CH₃); 3.14 (6H, q, J=7.2 Hz, —CH₂—CH₃); 3.39 (2H, AB, S—CH₂); 4.09 (2H, AB, —CH₂—thiadiazole); 5.08 (1H, d, J=4.5 Hz, H₆); 5.16-5.33 (2H, m, O—CH₂-pyridone); 5.71 (1H, d, J=4.5 Hz, H₇); 6.55 (1H, S, pyridonyl-H); 7.01 (1H, s, pyridonyl-H); 7.43 (1H, S, thiazolyl-H); 8.66 (1H, s, thiadiazolyl-H).

We claim:

1. The nitrate salt of (6R,7R)-7-{[2-(2-amino-4-thiazolyl)]-2-oxoacetamido}-3-(1,2,3-thiadiazol-5-yl)thiomethyl-3-cephem-4-carboxylic acid of formula I

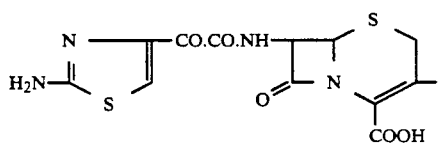

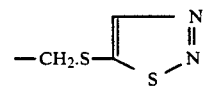

* * * * *